US009955991B2

(12) United States Patent
Riva

(10) Patent No.: US 9,955,991 B2
(45) Date of Patent: May 1, 2018

(54) DEVICE FOR ENDOSCOPIC RESECTION OR REMOVAL OF TISSUE

(75) Inventor: Raffaele Riva, Lugano (CH)

(73) Assignee: FRII S.A., Luxembourg (LU)

( * ) Notice: Subject to any disclaimer, the term of this patent is extended or adjusted under 35 U.S.C. 154(b) by 0 days. days.

(21) Appl. No.: 13/378,674

(22) PCT Filed: Jun. 14, 2010

(86) PCT No.: PCT/IB2010/001414
§ 371 (c)(1),
(2), (4) Date: Jan. 23, 2012

(87) PCT Pub. No.: WO2010/146432
PCT Pub. Date: Dec. 23, 2010

(65) Prior Publication Data
US 2012/0130165 A1 May 24, 2012

(30) Foreign Application Priority Data

Jun. 16, 2009 (CH) ...................... 0941/09

(51) Int. Cl.
*A61B 17/32* (2006.01)
*A61B 17/00* (2006.01)
(52) U.S. Cl.
CPC ...... *A61B 17/32002* (2013.01); *A61B 2017/0023* (2013.01); *A61B 2017/0046* (2013.01);
(Continued)
(58) Field of Classification Search
CPC ...... A61B 17/32002; A61B 2017/0023; A61B 2017/0046; A61B 2017/005; A61B 2017/00734
(Continued)

(56) References Cited

U.S. PATENT DOCUMENTS 3,452,741 A * 7/1969 Schaffer ............. A61B 10/0291
30/241
3,797,497 A 3/1974 Crim
(Continued)

FOREIGN PATENT DOCUMENTS

DE 102006033439 A1 1/2008
EP 0700663 A2 3/1996
(Continued)

OTHER PUBLICATIONS

International Search Report, dated Nov. 11, 2010, from corresponding PCT application.
(Continued)

*Primary Examiner* — Diane Yabut
*Assistant Examiner* — Martin T Ton

(57) ABSTRACT

A device (1) for treatments of endoscopic resection/removal of tissues, includes: a handpiece apt to be held by an user; an external tubular element (3) having a proximal end, a distal end and a cutting aperture disposed at the distal end; an internal tubular element (4) apt to be pivotally housed in the external tubular element (3) and having a proximal end, a distal end and a cutting tip at its distal end; guide element (5) for rotating and/or oscillating the internal tubular element (4) with respect to the external tubular element (3); the guide element including an electric motor. At least one between the handpiece (2) and the guide element (5) is disposable.

12 Claims, 3 Drawing Sheets

(52) U.S. Cl.
CPC .............. *A61B 2017/00734* (2013.01); *A61B 2217/005* (2013.01)

(58) Field of Classification Search
USPC .................................................. 606/167, 180
See application file for complete search history.

(56) References Cited

U.S. PATENT DOCUMENTS

| | | | |
|---|---|---|---|
| 3,995,619 A * | 12/1976 | Glatzer | 600/550 |
| 4,050,528 A * | 9/1977 | Foltz et al. | 173/217 |
| 4,217,964 A | 8/1980 | Eaton | |
| 4,649,919 A * | 3/1987 | Thimsen et al. | 606/80 |
| 4,867,155 A | 9/1989 | Isaacson | |
| 5,163,433 A | 11/1992 | Kagawa et al. | |
| 5,372,602 A | 12/1994 | Burke | |
| 5,376,089 A * | 12/1994 | Smith | A61B 18/1402 200/505 |
| 5,490,860 A | 2/1996 | Middle | |
| 5,492,527 A | 2/1996 | Glowa | |
| 5,505,210 A | 4/1996 | Clement | |
| 5,669,921 A | 9/1997 | Berman et al. | |
| 5,759,185 A * | 6/1998 | Grinberg | A61B 17/1615 606/180 |
| 5,796,188 A * | 8/1998 | Bays | 310/50 |
| 5,810,809 A | 9/1998 | Rydell | |
| 5,849,023 A | 12/1998 | Mericle | |
| 5,893,858 A * | 4/1999 | Spitz | 606/170 |
| 6,689,146 B1 * | 2/2004 | Himes | 606/167 |
| 2003/0163134 A1 | 8/2003 | Riedel | |
| 2003/0181934 A1 | 9/2003 | Johnston | |
| 2004/0073195 A1 | 4/2004 | Cucin | |
| 2004/0092992 A1 * | 5/2004 | Adams et al. | 606/180 |
| 2005/0159752 A1 * | 7/2005 | Walker et al. | 606/80 |
| 2007/0010823 A1 | 1/2007 | Kucklick | |
| 2008/0208233 A1 | 8/2008 | Barnes et al. | |
| 2008/0234715 A1 | 9/2008 | Pesce et al. | |

FOREIGN PATENT DOCUMENTS

| | | |
|---|---|---|
| GB | 2087239 A | 5/1982 |
| WO | WO9632894 A1 | 0/0000 |
| WO | WO2004028351 A2 | 0/0000 |
| WO | WO2008011308 A2 | 0/0000 |
| WO | 96/29014 A1 | 9/1996 |
| WO | WO99/13790 | 3/1999 |
| WO | WO03/079911 A1 | 10/2003 |
| WO | WO2012/176304 A1 | 12/2012 |

OTHER PUBLICATIONS

Search Report of CH priority application No. CH00941/09 dated Aug. 28, 2009.

* cited by examiner

DEVICE FOR ENDOSCOPIC RESECTION OR REMOVAL OF TISSUE

BACKGROUND OF THE INVENTION

The present invention relates to a device for treatments of endoscopic resection/removal of tissues. In particular, the invention relates to an endoscopic device for treatments of resection of soft tissue or osseus tissue (with relative removal of the fragments produced by such an action).

As an alternative to the traditional surgery, which requires a relatively wide incision to access to the surgical site inside the human body, the endoscopic procedures utilize natural accesses or as an alternative the creation of small portals (minimal tissular incisions); therefore often reference is made to the endoscopic surgery with the term of mini-invasive surgery. The two main advantages of the endoscopic surgery are the more rapid healing of the tissues after the surgical operation and the lesser exposition of internal tissues to the risk of infection. The technological developments in this surgical field, also defined "closed", have led to the realization of many minimally invasive instruments, as the access to the surgical site is made through one or more portals. Such instruments must be sufficiently elongated and smooth to permit the entrance and the use with a minimum trauma for the surrounding tissues.

A portion of the instrument, usually indicated as "distal portion", is so conceived in order to have access to the surgical site; the opposite portion, usually indicated as "proximal portion", remains at the outside of the body of the patient. The distal portion of the instrument is typically provided for treating the tissue with which it comes in contact, its shape and its dimensions being therefore properly studied in function of the particular surgical operation to which it is destined.

The proximal portion is instead provided with a mechanism to control from the outside of the body of the patient the above function. The motorized endoscopic surgical instruments, used in the "closed" surgery, often identified as endoscopic "shavers", are typically made by a pair of coaxial tubular concentrically disposed elements: an external element ending distally with an aperture or "cutting window" and a rotary internal element having a sharp surface at the cutting window. The rotary action of the internal tubular element produces by abrasion the removal or the finishing of the tissue, this process being defined as "resection".

As in each surgical action, also in the endoscopic surgery the presence of two well distinct fields is provided: the sterile field, the one in close contact with the patient, whereby the surgeon will perform his operation, and the one definitely separated from the patient and from any object coming in contact with it. Only suitably treated personnel and instruments can access to the sterile field (sterilization processes for the instruments, washing pre-operatory processes and adoption of protective aids for the personnel, as gloves and coats); all that can not enter in contact with the sterile field must rigorously remain outside of it.

DESCRIPTION OF THE RELATED ART

US2007/0010823 describes a "shaver" for arthroscopic operations and a system for providing the suction and the irrigation during a medical procedure with the above "shaver".

U.S. Pat. No. 5,669,921 describes a cutting device comprising:

an elongated external tube having a proximal end, a distal end and at said proximal end a bushing to permit the attachment of the external tube to an electrically fed sleeve; and an elongated internal tube apt to be received in said external tube, having a proximal end, a distal end, an internal aperture at said distal end, a cutting tip and a bushing disposed at the proximal end, the bushing permitting the connection of the internal tube to guide means for the cutting device.

SUMMARY OF THE INVENTION

The Applicant has noted that in the endoscopic "shavers" actually existing and/or in those described above the internal tubular element is brought in rotation and controlled by a handpiece having internally a small electric motor: the actuation and control are made either by pushbuttons positioned on the handpiece itself or by pushbuttons positioned on a pedal board. In both cases the power and the control signals arrive at the handpiece through a wire connected with an external bracket. This "bracket" is usually disposed on a trolley sufficiently distant from the operation field in order not to contaminate the sterile field. The handpiece (which comes in contact with the sterile field) undergoes a sterilization treatment before each surgical operation; the bracket having to remain out of each contact with the sterile zone, is housed out of the aforesaid field; in the actually existing systems, a connection wire is provided between handpiece and "bracket". Such connection wire before each use is treated in order to render it completely sterile and at the preparation of the surgical operation it is assembled from one side with the (sterile) handpiece and from the other side with the (non sterile) bracket. In the actually existing "shavers" the handpiece is made of a metallic material, so it has a non negligeable weight, and the connection wire has a weight and encumbrance such to limit the handling of the operator.

The personnel of the operation room which is responsible for the treatment and the management of the instrument at the end of each operation has to perform the washing (with suitable disinfectants and detergents) and then the sterilizing of the resterilizable parts (handpiece and wire); the cleaning and the sterilization negatively affect the useful life of the sterilizable components.

The personnel of the operation room must further perform the storing in suitable containers which guarantee the sterility, with a consequent waste of time and space consumption.

Nevertheless the personnel of the operation room must perform the maintenance of the non sterilizable components, i.e. the bracket and the pedal board if present, by making periodical inspections which can require more complex technical interventions by qualified personnel.

The Applicant has found that with a device for treatments of endoscopic resection/removal of the tissues providing at least an essential portion of the disposable device, it can be avoided that the operation personnel of the treatment and the management of the device perform at the end of each operation the washing (with suitable disinfectants and detergents) and then the sterilizing of the handpiece and the wire.

In one of its first aspects, the invention concerns a device for treatments of endoscopic resection/removal of tissues comprising:

a handpiece apt to be held by an user;

an external tubular element comprising a proximal end, a distal end and a cutting aperture disposed at said distal end;

an internal tubular element apt to be pivotally received in said external tubular element and comprising a proximal end, a distal end and a cutting tip at its distal end;

guide means for rotating and/or oscillating said internal tubular element with respect to said external tubular element;

characterized in that at least one of said handpiece and said guide means is disposable.

With the term "disposable" in the present description and in the following claims it is obvious that the portion of the shaver so indicated is used for an only endoscopic operation or for part of an endoscopic operation at the end of which it is removed and no more utilized.

The personnel of the operation room making the treatment and management of the instrument has not to perform at the end of each operation the washing (with suitable disinfectants and detergents) and then the sterilizing of the resterilizable parts.

The cleaning and sterilization of at least some parts of the shaver are avoided, with a relative lesser use of operation personnel, time and space.

The present invention, in the aforesaid aspect, can have at least one of the preferred features which are described in the following.

Advantageously, the guide means comprise electric feeding means for the electric motor.

According to a preferred aspect, the feeding means are contained inside the handpiece.

According to an alternative aspect, the feeding means are outside of the handpiece.

Preferably, only the handpiece is disposable. In this way, the more expensive portion of the device is recovered.

Advantageously the guide means are contained inside a body, insertable in a removable way into the handpiece.

Preferably the body is tight.

In order to permit a more rapid and easy extraction of the guide means with respect to the handpiece, the handpiece can comprise a distal portion supporting the external and the internal tubular element and a proximal portion engageable in a removable way with the distal portion.

Advantageously the guide means comprise a control unit contained inside the body. By providing the control unit inside the body, the manoevrability and the precision of the device are further improved.

The control unit can comprise at least one electronic circuit to regulate the functions and the speed of the electric motor and of a plurality of pushbutton controls placed on the external surface of said guide means, in a position corresponding to pushbuttons of a flexible material provided on the external surface of the handpiece.

Preferably, the device can comprise a transmission group of the motion actuated by the electric motor for rotating the internal tubular element with respect to the external tubular element.

Advantageously, the transmission group of the motion can comprise at least a shaft pivotally supporting the internal tubular element and at least a control pinion which rotates the shaft, actuated by the electric motor.

Preferably, the device can comprise a suction and cooling circuit having a connection for a suction apparatus, and at least a duct guiding a cooling fluid inside the internal tubular element and a suction regulating device.

Advantageously the suction and cooling circuit has a heat exchange portion with said electric motor for limiting the heating of the electric motor. Preferably the suction regulating device comprises a tap and a lever for controlling the tap from outside.

Advantageously the electric motor is a brushless motor.

Further features and advantages of the invention will be more evident from the detailed description of some preferred but non exclusive embodiments, of a device for treatments of endoscopic resection/removal of tissues, according to the present invention.

BRIEF DESCRIPTION OF THE DRAWING FIGURES

Such description will be exposed here in the following with reference to the annexed drawings, given only for an indicating and therefore not limiting aim, in which.

DETAILED DESCRIPTION OF THE INVENTION

Figure 1:
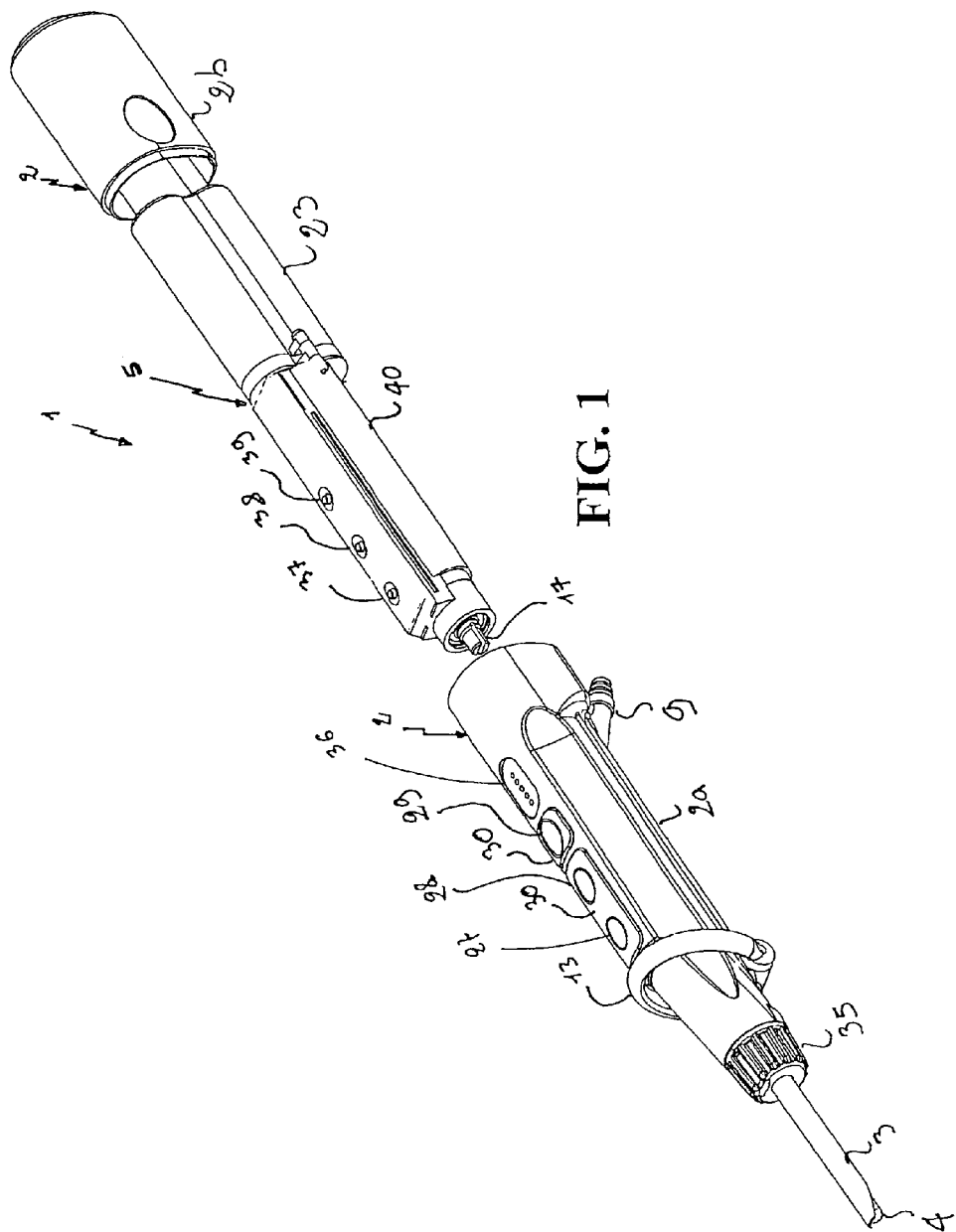
FIG. 1 is a schematic exploded view of a preferred embodiment of the device for treatments of endoscopic resection/removal of tissues, according to the present invention.
Figure 2:
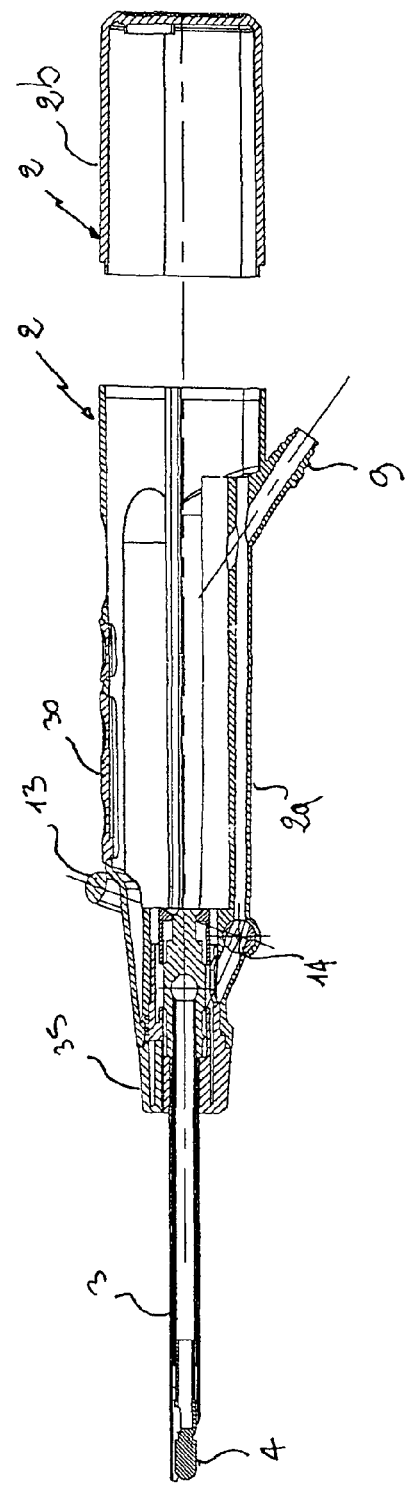
FIG. 2 is a sectional side schematic view of the handpiece of the device for treatments of endoscopic resection/removal of tissues shown in FIG. 1.
Figure 3:
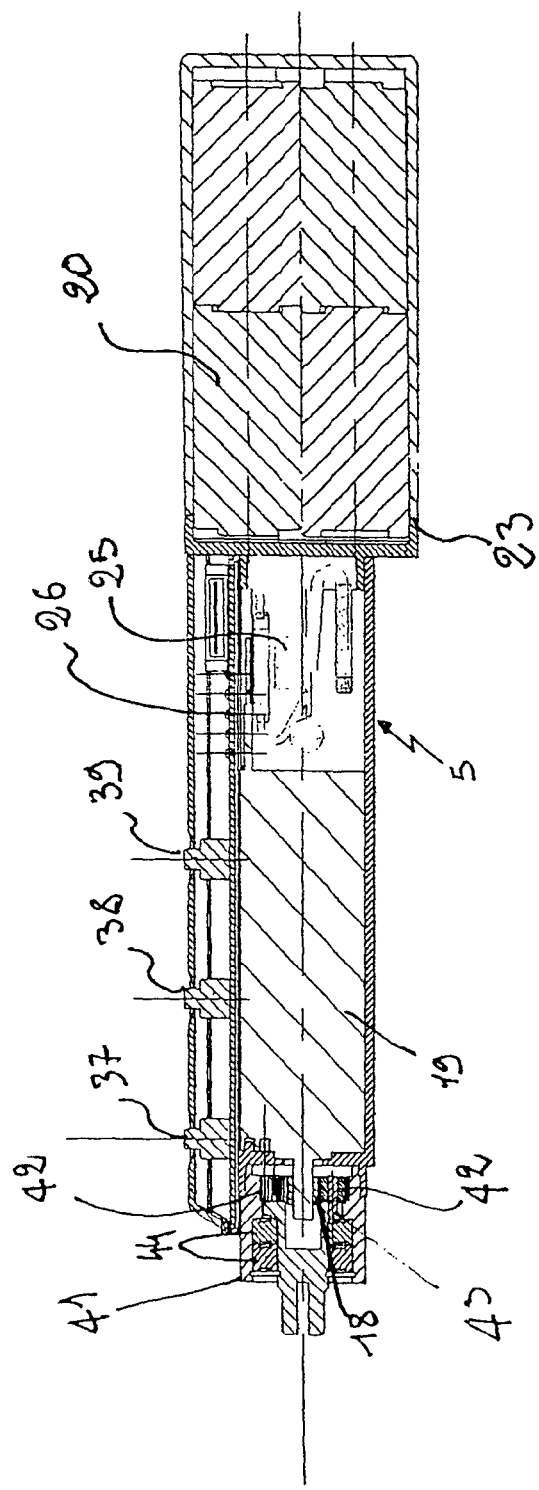
FIG. 3 is a sectional schematic view of an internal portion of the device in FIG. 1.

With reference to FIGS. 1-3, a device for treatments of endoscopic resection/removal of tissues is indicated with the reference character 1.

The device for treatments of endoscopic resection/removal of tissues 1 comprises a handpiece 2 apt to be held by an user, an external tubular element 3, an internal tubular element 4 and guide means 5 for rotating and/or oscillating the internal tubular element 4 with respect to the external tubular element 3.

The external tubular element 3 comprises a proximal end, a distal end and an aperture and/or cutting window disposed at the distal end.

The internal tubular element is shaped and dimensioned in order to be pivotally housed in the external tubular element 3 and it comprises a proximal end, a distal end and a cutting tip at its distal end, facing the cutting window. The pivotal action of the internal tubular element 4 produces by abrasion the removal or the finishing of the tissue, and this process is defined as "resection".

The guide means 5 comprise an electric motor 19 and electric feeding means 20 for the electric motor 19. The guide means according to an important aspect of the invention are reusable, whereas the handpiece is disposable and single-used. To this aim the guide means 19 are contained inside a suitable body 40 which can be completely housed inside the handpiece 2. In this way, the more expensive portion of the device can be recovered.

In order to permit an easy and rapid extraction of the guide means 5 with respect to the handpiece 2, the handpiece 2 can comprise a distal portion 2a, supporting the external tubular elements 3 and the internal tubular elements 4 and a proximal portion 2b engageable in a removable way with the distal portion 2a.

The ability to realize some parts, such as the handpiece 2, the external tubular elements 3 and the internal tubular elements 4 which are disposable, i.e. single-used, reduces remarkably the problems related to the storing and sterilization of such parts by the personnel of the operation room.

Furthermore, the ability to insert inside body 40 some functional parts of the device, in particular the electric motor 19 and the electric feeding means 20, permits to increase remarkably the manoevrability and the precision of motion of the device according to the present invention, with respect to the cutting devices for arthroscopy present in the market.

The electric motor 19 is preferably a brushless type motor, but another type of electric motor with suitable dimensions and similar power could be apt to this aim. The motor 19 is able to rotate at a speed comprised between 400 and 4000 revolutions per minute.

The electric motor 19 is controlled by a unit that controls each function of the device 1, i.e. the starting, the rotation or the simple oscillation of the internal tubular element 4 with respect to the external tubular element 3 and the pivotal speed of the internal tubular element 4.

Also the control unit is provided inside said body.

The control unit comprises at least a main electronic circuit 26, supported by an electronic support circuit and by an electronic auxiliary circuit 25.

The main electronic circuit 26 is connected to pushbutton controls 37; 38, 39 which permit to select from the outside the type of instruction to send to the main electronic circuit 26, i.e. the on or off-switching of the device 1, the type of oscillation/rotation of the internal tubular element 4 and the pivotal speed.

Advantageously, a rubber protection 30 can be provided for the aforesaid pushbutton controls 27; 28, 29, placed in a position corresponding to pushbutton controls 37, 38, 39.

The device can have some devices for the control of the speed by the user. To this aim, the device in figure shows five LEDs 36 connected to the control unit in order to indicate the set pivotal speed.

As can be seen in FIG. 1, the external tubular element through a locknut 35 is connected to the handpiece 2.

Inside the body a group of transmission of motion is also present, comprising a satellite reducer.

In detail, the internal tubular element 4 is brought by a shaft 17 which through a motor pinion 18 functionally connects the internal tubular element with the electric motor 19.

Between the motor pinion 18 and the shaft 17 the box 45 of the satellite reducer is also provided, comprising the satellites 42 and the satellite support shaft 43.

The group for the transmission of motion also has two radial bearings 44, radially juxtaposed, between the motor shaft 17 and the box 45 of the satellite reducer.

The motor pinion 18 engages with the satellites 42 which, through the satellite support shaft 43, transfer the motion to the shaft 17.

Alternatively to the group of coaxial transmission just described a group of transmission is provided with a chain of gears with the provision in any case of the shaft 17 functionally connected to the internal tubular element and through a motor pinion 18 to the electric motor 19.

In this case therefore between the motor pinion 18 and the shaft 17 pinions of first reduction could be provided, a rotary pin of the pinions of first reduction and trimming washers.

The shaft 17 could be pivotally supported by a bearing and a bush, at the distal axial end of the shaft 17.

The electric feeding means 20 of the preferred embodiment shown in FIGS. 1-3 are represented by rechargeable alkaline or lithium batteries, but any other kind of batteries could be used to this aim without departing from the protection field of the invention.

The batteries are contained inside a container 23 provided at the more proximal end of the body.

The container 23 has suitable electric connections in order to feed the electric motor 19 and a non mobile cover for substituting the batteries and for inspection of the electric connections.

Preferably the container 23 is also tight.

The electric motor 19 is housed inside the body 40 which axially extends inside the handpiece 2.

The body 40 centrally contains the motor pinion 18, in a proximal position with respect to the control unit controlling and regulating the motor 19 and frontally the group of transmission of motion.

Preferably, the device 1 according to the present invention can comprise a suction and cooling circuit comprising a connection 9 for a suction apparatus, outside the handpiece 2 and not shown in the figures, at least a duct which guides from said connection 9 the cooling fluid of the internal tubular element 4 and a device for regulating the feeding of the cooling fluid to the internal tubular element.

The device for regulating the feeding of the cooling fluid to the internal tubular element comprises a tap 14 and a lever 13 to control the tap 14 from outside. Advantageously the cooling circuit has a heat exchange portion with said electric motor 19 in order to limit its heating.

To this aim, the heat exchange portion axially extends inside the handpiece 1 in order to axially pass through the entire motor 19.

According to an advantageous aspect of the present invention the handpiece 2 is tight.

According to an alternative aspect of the present invention the feeding means are placed inside the handpiece, and in this case it is possible for example to provide a connection for an external electric source, such as a socket.

According to another aspect of the present invention the entire device 1 is disposable and single-used, in order to guarantee the perfect sterilization of the instrument.

Furthermore, it can be avoided that the personnel of the operation room which performs the treatment and management of the device must perform the washing (with suitable disinfectants and detergents) and then the sterilization of parts of the device.

The personnel of the operation room must not perform the storing of the device in suitable containers which can guarantee the sterilization, with a consequent consumption of time and space.

Nevertheless the personnel of the operation room must not perform anymore the maintenance of non sterilizable components.

The invention claimed is:

1. A device for treatments of endoscopic resection and removal of tissues, comprising:
    a disposable handpiece, the handpiece comprising a distal portion and a proximal portion that is directly engaged in a removable way with the distal portion, the handpiece having a longitudinal length with a longitudinal axis, with the distal portion and the proximal portion being axially aligned along the longitudinal length and the longitudinal axis;
    a disposable external tubular element comprising a proximal end and a distal end, the distal end defining a cutting window and including a first distal edge portion being a distalmost edge portion and a second distal edge portion proximal to the first distal edge portion, and a curved portion between said first and second distal edge portions, the distal end of the external tubular element being located on the longitudinal axis of the handpiece, the proximal end of the external tubular element being located within and terminating in a distal end of the distal portion of the handpiece;

a disposable internal tubular element pivotally received in said external tubular element and comprising a proximal end, a distal end and a cutting tip at the distal end of the disposable internal tubular element, the distal end of the internal tubular element being located on the longitudinal axis of the handpiece and including a solid cylindrical outer surface with a substantially constant outer diameter and the proximal end of the internal tubular element being located within and terminating in the distal portion of the handpiece, wherein the distal end of the internal tubular element extends longitudinally past the second distal edge portion of the disposable external tubular element but not longitudinally past the first distal edge portion of the disposable external tubular element, wherein the internal tubular element is releasably supported within the distal portion of the handpiece;

an externally accessible locknut that connects the external tubular element to the distal portion of the handpiece;

a guide that rotates said inner tubular element with respect to said external tubular element such that a pivotal action of the inner tubular element produces, by abrasion, removal of tissue thereby resecting the tissue, wherein said guide comprises a control unit and an electric motor longitudinally aligned with an electric feeding member for said electric motor, said electric feeding member extending axially with respect to said electric motor in said longitudinal direction; and a body that extends axially inside both the distal portion and the proximal portion of the handpiece, the body housing said electric motor, said electric feeding member and said control unit, said control unit comprising at least a main electric circuit connected to internal pushbuttons positioned on the body and which permit selection of instructions to send to the main electronic circuit from outside of the handpiece, wherein, i) during use of said device, said distal portion of the handpiece includes external pushbuttons on an outer surface thereof, each external pushbutton disposed in an external position corresponding to an internal position of a corresponding one of said internal pushbuttons such that said external pushbuttons enable said selection of instructions to send to the main electric circuit from outside of the handpiece, and ii) when said distal portion of the handpiece, while supporting the internal tubular element and the external tubular element, is disengaged and removed from the proximal portion of the handpiece, said body is removable from and interchangeable with respect to the distal and proximal portions of the handpiece so that said body containing said electric motor, said control unit and said electric feeding member is reusable by removing said body from said handpiece prior to disposal of said handpiece, the internal tubular element, and the external tubular element.

2. The device according to claim 1, wherein said main electric circuit regulates functions and speed of said electric motor.

3. The device according to claim 1, further comprising a group for the transmission of motion from said electric motor in order to rotate said internal tubular element with respect to said external tubular element.

4. The device according to claim 3, wherein said group for the transmission of motion comprises at least a shaft pivotally supporting said internal tubular element and at least a motor pinion to rotate, actuated by said motor, said shaft.

5. The device according to claim 1, further comprising a cooling circuit comprising a connection for a suction apparatus, at least a duct which guides cooling fluid to said internal tubular element and a device for regulating the motion.

6. The device according to claim 5, wherein said cooling circuit has a portion of heat exchange with said electric motor to limit the heating of said electric motor.

7. The device according to claim 6, wherein said device for regulating the suction comprises a tap and a lever to control from outside said tap.

8. The device according to claim 5, wherein said device for regulating the suction comprises a tap and a lever to control from outside said tap.

9. The device according to claim 1, wherein said electric motor is a brushless motor.

10. The device according to claim 1, wherein, said body comprises a distal portion separated from a proximal portion by a partition wall shared by the distal and proximal portions, the partition wall including electric connections that feed the electric motor from the electric feeding member, the proximal portion defining a container having a removable cover adjacent the partition wall, the electric feeding member for the electric motor are batteries located within a container with one end of the batteries against the electric connections, the container being located at a proximal end of said body, the batteries being replaceable when the cover of the container is removed, a distal end of the electric motor comprises a motor pinion, and the motor pinion functionally connects the internal tubular element with the electric motor and during use of said device, the electric motor rotates at the speed between 400 and 4000 revolutions per minute.

11. A device for treatments of endoscopic resection and removal of tissues, comprising:

a disposable handpiece, the handpiece comprising a distal portion and a proximal portion that is directly engaged in a removable way with the distal portion, the handpiece having a longitudinal length with a longitudinal axis, with the distal portion and the proximal portion being axially aligned along the longitudinal length and the longitudinal axis;

a disposable external tubular element comprising a proximal end and a distal end, the distal end defining a cutting window and including a first distal edge portion being a distalmost edge portion and a second distal edge portion proximal to the first distal edge portion, and a curved portion between said first and second distal edge portions, the distal end of the external tubular element being located on the longitudinal axis of the handpiece, the proximal end of the external tubular element being located within and terminating in a distal end of the distal portion of the handpiece;

a disposable internal tubular element pivotally received in said external tubular element and comprising a proximal end, a distal end and a cutting tip at the distal end of the disposable internal tubular element, the distal end of the internal tubular element being located on the longitudinal axis of the handpiece and including a solid cylindrical outer surface with a substantially constant outer diameter and the proximal end of the internal tubular element being located within and terminating in the distal portion of the handpiece, i) wherein the distal end of the internal tubular element extends longitudinally past the second distal edge portion, of the disposable external tubular element but not longitudinally past the first distal edge portion of the disposable external tubular element, wherein the internal tubular element is releasably supported within the distal portion of the handpiece;

an externally accessible locknut that connects the external tubular element to the distal portion of the handpiece;

a guide that oscillates said inner tubular element with respect to said external tubular element such that a pivotal action of the inner tubular element produces, by abrasion, removal of tissue thereby resecting the tissue, wherein said guide comprises a control unit and an electric motor longitudinally aligned with an electric feeding member for said electric motor and, said electric feeding member extending axially with respect to said electric motor in said longitudinal direction; and a body that extends axially inside both the distal portion and the proximal portion of the handpiece, the body housing said electric motor, said electric feeding member and said control unit, said control unit comprising at least a main electric circuit connected to internal pushbuttons positioned on the body and which permit selection of instructions to send to the main electronic circuit from outside of the handpiece, wherein, i) during use of said device, said distal portion of the handpiece includes external pushbuttons on an outer surface thereof, each external pushbutton disposed in an external position corresponding to an internal position of corresponding one of said internal pushbuttons such that said external pushbuttons enable said selection of instructions to send to the main electric circuit from outside of the handpiece, and ii) when said distal portion of the handpiece, while supporting the internal tubular element and the external tubular element, is disengaged and removed from the proximal portion of the handpiece, said body is removable from and interchangeable with respect to the distal and proximal portions of the handpiece so that said body containing said electric motor, said control unit and said electric feeding member are reusable by removing said body containing said electric motor and said electric feeding member from said handpiece prior to disposal of said handpiece, the internal tubular element, and the external tubular element.

12. The device according to claim 11, wherein the solid cylindrical outer surface with a substantially constant outer diameter produces said abrasion.

* * * * *